United States Patent [19]

Nelson

[11] 4,338,936
[45] Jul. 13, 1982

[54] DEVICE AND METHOD FOR DELIVERING SOLID MEDICATION TO AN EYE

[76] Inventor: Byron Nelson, 3521 Perada, Walnut Creek, Calif. 94598

[21] Appl. No.: 201,180

[22] Filed: Oct. 27, 1980

[51] Int. Cl.³ .......................................... A61M 11/00
[52] U.S. Cl. .................................. 128/266; 128/231
[58] Field of Search ................. 128/265, 266, 203.15, 128/231, 232, 249

[56] References Cited

U.S. PATENT DOCUMENTS 465,484  12/1891  Magoris ............................. 128/266
903,098  11/1908  Katzenberger ..................... 128/232

FOREIGN PATENT DOCUMENTS 17962  of 1890  United Kingdom ........... 128/203.15

Primary Examiner—Henry J. Recla
Attorney, Agent, or Firm—Bielen & Peterson

[57] ABSTRACT

A device for delivering finely divided solid medication to any eye which uses a flexible container having an air chamber and an opening leading to the air chamber. An element holds a predetermined dose of the finely divided solid medication. A filter provides a solid barrier to the interior of the air chamber and separates the finely divided material from the same. The airborne medication is directed to the proper portion of the eye.

5 Claims, 3 Drawing Figures

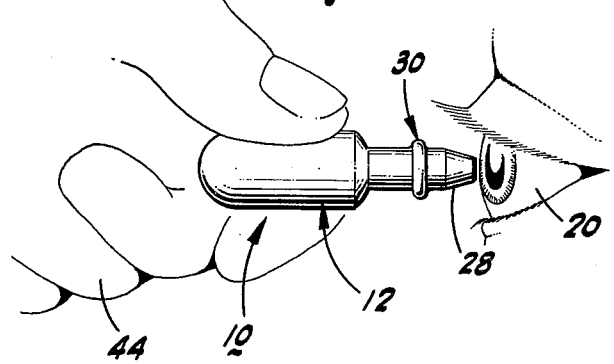
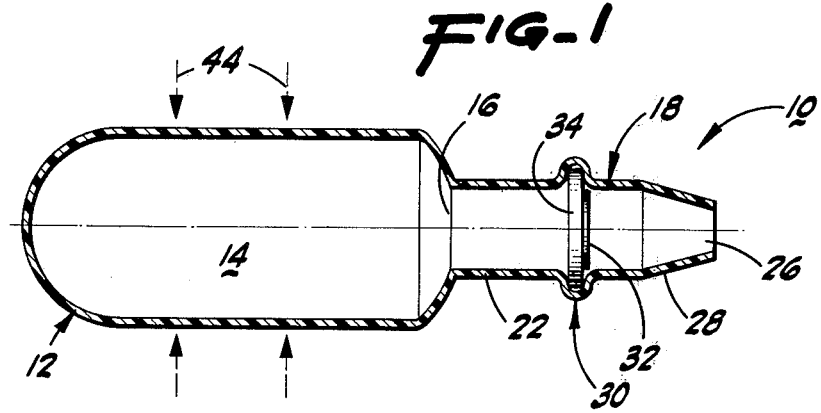
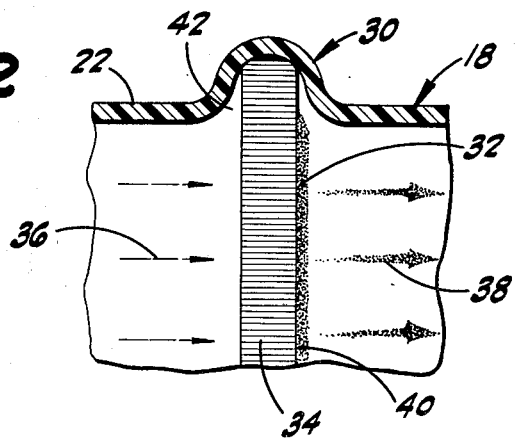

DEVICE AND METHOD FOR DELIVERING SOLID MEDICATION TO AN EYE

BACKGROUND OF THE INVENTION

The present invention relates to a novel device and method for delivering medication to an eye which is particularly useful for transporting finely divided solid medication to an eye.

In the past, medications have been delivered to the eye in liquid form by the use of an eye dropper. The typical eye dropper delivers approximately 50 microliters in each drop. Unfortunately, the typical human eye can only tolerate 25 to 35 microliters of fluid in the tear film which lies against the cornea of the eye. In addition, aqueous medications must be dissolved is a solvent, and buffered to the proper pH range to avoid injury to the eye. In addition, preservatives must be added to the liquid medication to prevent deterioration of the same before delivery to the eye.

The delivery of medication in a finely divided form would eliminate the extensive preparation of the medication in liquid form and would be a great advance in the art of opthalmic treatment.

SUMMARY OF THE INVENTION

In accordance with the present invention a novel and useful device and method for delivering solid medications to an eye is provided.

The device of the present invention uses finely divided solid medication in a specific dose which is easily dissolved or dispersed by the existing tear film on the eye. The device includes as one of its elements a flexible container having an air chamber therewithin and an opening leading to the air chamber. The flexible container is meant to be squeezed, causing evacuation of the air from this chamber and causing the air to be passed through the opening leading to the air chamber.

The device also includes means for holding a predetermined dose of the finely divided solid medication in the path of the air leaving the chamber before arrival of the air at the eye. Filter means intended for preventing the finely divided solid medication from entering the air chamber of the flexible container is placed at the opening communicating with the air chamber. Such filter means serves as a solids barrier against entry of the finely divided solid medication into the chamber. In one embodiment of the invention the filter means may serve as means for holding a predetermined dose of the finely divided solid medication by replacement of the same on one side of the filter outside the confines of the air chamber.

The device may also include means for directing air from the air chamber to the eye. Such means may take the form of an elongated member and may also provide an enlargement or space for holding the filter means.

The present invention may be deemed also to include a method for delivering solid medication to an eye which uses the steps of filling a chamber, having an opening, with air and placing the first side of a filter adjacent the opening to form a solids barrier to the air chamber. A predetermined dose of finely divided solid medication is placed adjacent the second side of the filter. The air is evacuated from the chamber with a certain velocity and directed through the filter. In the case where the container is a flexible container, mere squeezing will create this effect. At least a portion of the finely divided solid medication is carried by the air which has passed through the filter and directed to the eye. The natural tear film in the eye will dissolve or disperse the medication.

It may be apparent that a novel and useful device and method for delivering finely divided solid medication to an eye has been described.

It is therefore an object of the present invention to provide a device and method which employs an air vehicle to direct small amounts of solid medication into the corneal conjunctival area of an eye.

It is another object of the present invention to provide a device and method for delivering the finely divided solid medication to an eye which employs the natural precorneal tear film as a wetting and spreading agent.

It is yet another object of the present invention to provide a device and method for delivering finely divided solid medication to an eye which employs a disposable item which may be easily sterilized and which delivers the proper amount of medication to an eye.

It is another object of the present invention to provide a device and method for delivering finely divided solid medication to an eye which eliminates the need for mixing or compounding medication with inert or potentially interfering substances in the medical treatment of an eye.

The invention possesses other objects and advantages especially as concerns particular characteristics and features thereof, which will become apparent as the specification continues.

BRIEF DESCRIPTION OF THE DRAWINGS

FIG. 1 is a sectional view of the device.

FIG. 2 is an enlarged sectional view of a portion of the device showing the placement of the filter means.

FIG. 3 is a side elevational view of the device which illustrates a portion of the method of use of the device.

For a better understanding of the invention, reference is made to the following detailed description which should be referenced to the hereinabove described drawings.

DESCRIPTION OF THE PREFERRED EMBODIMENTS

Various aspects of the present invention will evolve from the following detailed description of the preferred embodiments thereof, which should be taken in conjunction with the hereinabove described drawings.

The invention as a whole is represented in the drawings by reference character 10. Device 10 includes a container 12 which includes an air chamber 14 therewithin. Container 12 may be constructed of a flexible material such as an acrylic polymer plastic or any other material which is capable of being sterilized by known methods. Container 12 includes an opening 16 which communicates with air chamber 14 and is intended for permitting the passage of air to and from chamber 14 of container 12.

With reference to FIG. 1, device 10 also includes means 18 for directing air from chamber 14 to eye 20. Means 18 may take the form of a hollow member 22 having a first opening, adjacent opening 16 of container 12, for communicating with air chamber 14. A second opening 26 and hollow member 22 is intended for placement adjacent eye 20, FIG. 3, and may include a nozzle 28 to increase the velocity of air passing through that section of hollow member 22.

The device also includes as one of its elements means 30 for holding a predetermined dose of finely divided solid medication 32. Means 30 supports medication 32 in the path of the air leaving chamber 14 before its arrival at eye 20. Medication 32 may be divided roughly to the 5 to 100 micron size, however, other size particles outside this range may serve equally as well in delivery of medication to eye 20. For example, it is anticipated that dilators, relaxants, miotics, antibiotics, and anti-inflammatory drugs presently used in liquid form may also be easily prepared in the finely divided solid form, by freeze-drying, dehydration, and the like. Solid medication 32 may also include a dispersing agent to prevent flocculation of the same when entering the tear film of eye 20. It is known that the tear film of a typical eye contains 25 to 35 microliters of fluid. Of course, the amount of solid medication 32 held by means 30 would be determined to correspond to the typical volume of tear fluid in the eye 20. Filter means 34 is placed such that a solid barrier is formed between second opening 26 of means 18 and air chamber 14 of container 12. Filter means 34 may be a Teflon filter such as the Fluoropor filter, 3 micron particle size, manufactured by the Millipore Corp. of Bedford, Massachusetts. Filter means 34 would prevent the passage of any solid medication 32 into air chamber 12 but permit the passage of air, shown by arrows 36 in FIG. 2, therethrough such that solid medication 32 is carried through means 18 to eye 20, arrows 38 of FIG. 2. In a sense, filter means 34 defines an extremity of air chamber 14 although filter means 34 may be located in hollow member 22 of means 18 for directing air to eye 20. Filter means 34 also includes, in the embodiments shown in FIGS. 1 through 3, a surface 40 which serves as means 30 for holding solid medication 32. It is anticipated that surface 40 would possess the necessary surface characteristics for causing the adherence of solid medication 32 thereto, such as a surface which produces static electricity. However, the adherence of solid particles 32 to surface 40 would not be of great enough force to resist the impact of air flowing from chamber 14, arrows 36, when the air is evacuated from chamber 14. It should be noted that in the case where container 12 is flexible, mere squeezing of container 12 will produce the evacuation of at least a portion of the air within chamber 14. Of course, other methods may be used to evacuate the air from chamber 14.

Filter means 34 may be located in hollow member 22 by the formation of an enlargement or recess 42, FIG. 2. Where hollow member 22 is flexible, filter means 34 may be press fitted into enlargement 42 for use.

With reference to FIG. 3, it may be seen that the device may be operated by the human hand 44 such that container 12 is squeezed producing a force, arrows 44, which evacuates the air previously filling chamber 14 therefrom. Air leaving chamber 14, arrows 36, pass through filter 42 and carry the solid medication 32 through hollow member 22 and opening 26 to eye 20. The device 10 is positioned as shown in FIG. 3 to deliver the solid medication to the tear film of the eye. Any force tending to push the finely divided solid medication into chamber 44 would be resisted by filter means 34. As previously discussed, the proper amount of solid medication 32 would be placed on surface 40 of filter 34 before use of device 10. Such loading of device 10 may take place long before use and may include the sealing of second opening 26 of hollow member 22 as well as the barricading of device 10 against any unwanted force on container 12. After use of device 10, it may be discarded, thus obviating the need for refilling and resterilizing.

While in the foregoing specification embodiments of the present invention have been set forth in considerable detail for the purposes of making a complete disclosure of the invention, it may be apparent to those of ordinary skill in the art that numerous changes may be made in such details without departing from the spirit and principles of the invention.

What is claimed is:

1. A device for delivering finely divided solid medication to an eye comprising:

a. a flexible container having an air chamber therewithin and an opening, communicating with said air chamber for passage of air to and from said chamber;

b. means adapted for directing air from said air chamber to the eye comprising a hollow member having a first opening communicating the interior thereof with said air chamber and an opening second opening adapted for placement adjacent the eye;

c. means intended for holding a predetermined dose of the finely divided solid medication in the path of the air leaving said chamber through said directing means before arrival of the air at the eye;

d. filter means intended for preventing the finely divided solid medication from entering the air chamber of the flexible container, said filter means defining an extremity of said air chamber, said filter means being located in said hollow member, said hollow member including an enlargement for holding said filter means.

2. The device of claim 1 in which said hollow member comprises a flexible elongated member.

3. The device of claim 1 in which said means for holding a predetermined dose of the finely divided solid medication in the path of the air leaving the chamber comprises said filter means including a surface having an affinity for the finely divided powder, said surface being located outside the air chamber extremity defined by said filter means.

4. A method of delivering finely divided solid medication to an eye comprising the steps of:

a. filling a chamber in a container with air, said container having an opening communicating with said chamber;

b. placing the first side of a filter having a first and second side adjacent said opening in said container to form a solids barrier to said air chamber, said second side of said filter including means for holding a predetermined dose of finely divided solid medication thereto;

c. placing a predetermined dose of the finely divided solid medication on the second side of said filter;

d. simultaneously evacuating at least a portion of the air from said chamber through said opening with a certain velocity, and directing the evacuated air through said filter, and carrying at least a portion of the finely divided solid medication in the moving air which has passed through said filter;

e. directing said air carried solid medication to the eye.

5. The method of claim 4 in which said step of filling a chamber in a container includes filling a chamber in a flexible container, and said step of evacuating at least a portion of the air from said chamber, includes squeezing said flexible container to cause said evacuation of air from said chamber.

* * * * *